(12) United States Patent
Berghmans et al.

(10) Patent No.: US 9,114,436 B2
(45) Date of Patent: Aug. 25, 2015

(54) METHOD FOR SORTING POTATO PRODUCTS AND SORTING APPARATUS FOR POTATO PRODUCTS

(75) Inventors: Paul Berghmans, Scherpenheuvel (BE); Christiaan Fivez, Wilsele (BE); Johan Speybrouck, Brussels (BE)

(73) Assignee: TOMRA SORTING NV, Leuven (BE)

( * ) Notice: Subject to any disclaimer, the term of this patent is extended or adjusted under 35 U.S.C. 154(b) by 423 days.

(21) Appl. No.: 13/258,276

(22) PCT Filed: Mar. 26, 2010

(86) PCT No.: PCT/BE2010/000025
§ 371 (c)(1),
(2), (4) Date: Sep. 21, 2011

(87) PCT Pub. No.: WO2010/108241
PCT Pub. Date: Sep. 30, 2010

(65) Prior Publication Data
US 2012/0021101 A1    Jan. 26, 2012

(30) Foreign Application Priority Data
Mar. 26, 2009   (BE) .................................. 2009/0192

(51) Int. Cl.
*B07C 5/36* (2006.01)
*B07C 5/342* (2006.01)
*G01N 33/02* (2006.01)

(52) U.S. Cl.
CPC ............... *B07C 5/368* (2013.01); *B07C 5/3427* (2013.01); *G01N 33/02* (2013.01)

(58) Field of Classification Search
CPC ...... B07C 5/34; B07C 5/3416; B07C 5/3422; B07C 5/3427; B07C 5/36; B07C 5/368; G01N 21/3563; G01N 33/02; Y10S 209/938; A01B 12/006
USPC .................................... 426/231; 209/576, 581
See application file for complete search history.

(56) References Cited

U.S. PATENT DOCUMENTS

| 4,634,881 | A | 1/1987 | Billion |
| 4,723,659 | A | 2/1988 | Billion |
| 2002/0011567 | A1* | 1/2002 | Ozanich ......................... 250/326 |
| 2010/0055259 | A1* | 3/2010 | Bourg, Jr. ..................... 426/231 |

FOREIGN PATENT DOCUMENTS

| DE | 4127903 A1 | 4/1993 |
| WO | WO 0100333 A1 | 1/2001 |

\* cited by examiner

*Primary Examiner* — Steven Leff
(74) *Attorney, Agent, or Firm* — Buchanan Ingersoll & Rooney P.C.

(57) ABSTRACT

The invention concerns a method and a sorting apparatus for sorting potato products that are moved in a product flow through a detection zone, whereby irregular products are detected in the product flow and are separated from the product flow, characterized in that a light beam having a wavelength of in between 350 and 450 nm is directed towards said products in said detection zone and wherein the intensity of the light that is irradiated by the products is detected in a detection band from 460 nm to 600 nm, wherein a product is qualified as an irregular product and is separated from the product flow when said intensity is below a predetermined value. Further, the invention also concerns a method and a device for detecting the presence of solanine in potato products by means of fluorescence.

17 Claims, 4 Drawing Sheets

METHOD FOR SORTING POTATO PRODUCTS AND SORTING APPARATUS FOR POTATO PRODUCTS

The invention concerns a method for sorting potato products which are being moved through a detection zone in a product flow, whereby unwanted products are detected in this product flow and are separated from the product flow.

According to the present state of the art, potato products are sorted by illuminating the potato products with one or several laser beams and by subsequently detecting the light which is scattered by the products or reflected directly. On the basis of this directly reflected or scattered light, the presence of any flaws in the products or of strange products is established. Such sorting systems are described for example in documents U.S. Pat. No. 4,723,659 and U.S. Pat. No. 4,634,881.

These known sorting systems for potato products are disadvantageous, however, in that laser beams with different wave lengths must be provided for the different flaws one wishes to find in the products or for the strange products one wishes to detect. Thus, the known sorting machines usually comprise several laser sources with different wave lengths, whereby for every wave length must be provided a corresponding detection system with detectors and accompanying diaphragms for directly reflected and scattered reflected light. Moreover, the use of several laser sources makes it necessary for the laser beams that are generated by the latter to be almost perfectly aligned.

Since, when sorting the potato products, the signals of all the detectors must be processed, the control unit of said sorting systems must process a huge amount of data.

Moreover, it was found that certain flaws in potato products cannot be detected, such as for example the presence of solanine in the products.

The invention aims to remedy these disadvantages by providing a method and a sorting machine which make it possible to detect the presence of flaws in the potato products or of strange objects in the product flow with a very small margin of error with a single beam of light. Said flaws may be for example the presence of eyes, offshoots or buds, rot, bruises, inner sugars, a brown coloured vascular bundle ring, etc. Moreover, the invention makes it possible to detect the presence of solanine in the potato products.

To this aim, in said detection zone, a beam of light with a wave length between 350 and 450 nm is directed to said products, and the intensity of the light which is emitted by the products is detected in a detection band of 460 to 600 nm. A product is thereby qualified as an undesirable product and separated from the product flow when said intensity is lower than a preset value.

Practically, said detection band is situated between 480 and 580 nm, and the presence of a fluorescence peak is detected in this detection band, whereby a product will be qualified as an undesirable product and will be separated from the product flow if said fluorescence peak is not present.

For the sorting of raw potato products, said detection band is advantageously situated between 540 and 570 nm, and the presence of a fluorescence peak is detected in this detection band, in particular a fluorescence peak having a wave length of some 560 nm. If this fluorescence peak is not present, a product will be qualified as an undesirable product and will preferably be separated from the product flow.

According to an interesting embodiment of the method according to the invention, potato products baked in vegetable oil are sorted by detecting the presence of a fluorescence peak in a detection band situated between 480 and 580 nm. In particular, the presence of a fluorescence peak having a wave length of some 520 nm is detected. If this fluorescence peak is not present, a product will be qualified as an undesirable product and it will be separated from the product flow.

Further, according to a special embodiment of the method according to the invention, the presence of glycoalkaloid, in particular of solanine, in said potato products is detected by detecting fluorescence, resulting from the incidence of said beam of light on the products in a red light spectrum. In particular, the intensity of the light which is emitted by the products is detected in a band of 600 nm to 700 or 750 nm. A product will thus be qualified as a product containing glycoalkaloid and it will be removed from the product flow if said intensity exceeds a preset value. Said fluorescence peak for detecting the presence of solanine is hereby preferably detected by a wave length of some 680 nm.

According to a preferred embodiment of the method according to the invention, said products are moved in the detection zone in front of a background element, whereby this background element extends over the entire width of the product flow, such that the beam of light will strike this background element whenever there is no product in the beam of light. The background element will hereby emit light having a wave length which corresponds to said detection band when said beam of light strikes the latter. Preferably, the background element will fluoresce in the wave length band wherever a good product has a fluorescence peak, whereas this background element will not fluoresce in the wave length band wherever the fluorescence peak for detecting the presence of solanine is situated.

The invention also concerns a sorting machine to apply the method according to the invention, whereby a light source is provided which generates a beam of light having a wave length situated in a band of 350 to 450 nm which strikes said products in the detection zone, whereby the sorting machine comprises a detector that is sensitive to green light having a wave length of 460 to 600 nm and which generates a detection signal as a function of the observed light intensity. This detector co-operates with a control system to control a removal device for the removal of unwanted products from the product flow when the light intensity observed by the detector is lower than a preset value.

Other particularities and advantages of the invention will become clear from the following description of some specific embodiments of the method and the sorting machine according to the invention. This description is given as a mere example and does not limit the scope of the claimed protection in any way; the figures of reference used hereafter refer to the accompanying drawings.

In the different drawings, the same reference figures refer to the same or analogous elements.

In the method according to the invention, potato products are sorted on the basis of fluorescence. It was found that when UV light with a wave length of 350 to 450 nm strikes the potato products, potato products without any flaws will emit light as a result of the fluorescence having a wave length which is mainly situated in the wave length band of 460 nm to 600 nm. Flaws which are present in the potato products or strange products in the product flow do not have said fluorescence. The flaws can usually be visually observed and consist for example of the presence of eyes, offshoots or buds, rot, bruises, inner sugars, a brown coloured vascular bundle ring, etc.

According to the invention, a product flow of potato products is moved through a detection zone where the products are illuminated with UV light. The intensity of the light which is emitted by the products as a result of the fluorescence is detected in a detection band of 460 nm to 600 nm. When the observed intensity in the detection zone is lower than a specific preset value for a product, it is assumed that there is no fluorescence peak, and the product concerned will be qualified as an undesirable product and if necessary it will be removed from the product flow. By an undesirable product is understood a strange component or a potato product with a flaw.

The fluorescence peak occurring as a result of the excitation by the light with a wave length between 350 and 450 nm is usually observed in a detection band of 480 to 580 nm, irrespective of the wave length of the exciting light beam.

For raw potato products, a detection band of 540 to 570 nm is preferably used. As is clear from FIG. 1, a fluorescence peak of some 560 nm will occur for raw peeled potato products when said beam of light is generated for example by a laser source with a wave length of 405 nm. In order to thus sort a product flow with said potato products, the presence of a fluorescence peak of some 560 nm is preferably detected.

Figure 2:
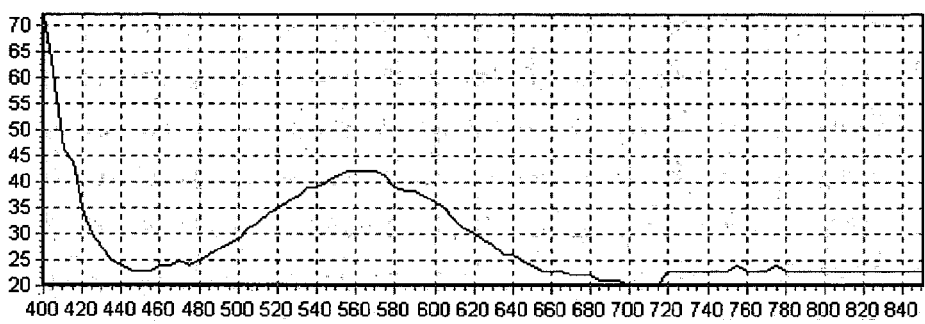
FIG. 2 represents the fluorescence spectrum of a potato peel when excited by a laser with a wave length of 405 nm.

Further, it was found that the potato peel has a fluorescence peak around practically the same wave length, such that the method according to the invention can also be used to detect for example flaws on the surfaces of unpeeled potato products. The fluorescence spectrum of potato peels is represented in FIG. 2.

However, the method according to the invention is particularly interesting for sorting potato products baked in vegetable oil. Such products may for example consist of thin, baked potato slices, in particular chips, or of baked potato slivers such as fries.

The vegetable oil in which the potato products are baked may for example be peanut oil, sunflower oil with a high olein content (HOSO), maize germ oil, frying oil, coleseed oil or sunflower oil. This vegetable oil preferably has a fluorescence peak of some 500 to 540 nm when being excited by UV light, in particular light having a wave length situated between 350 and 450 nm.

Figure 3:
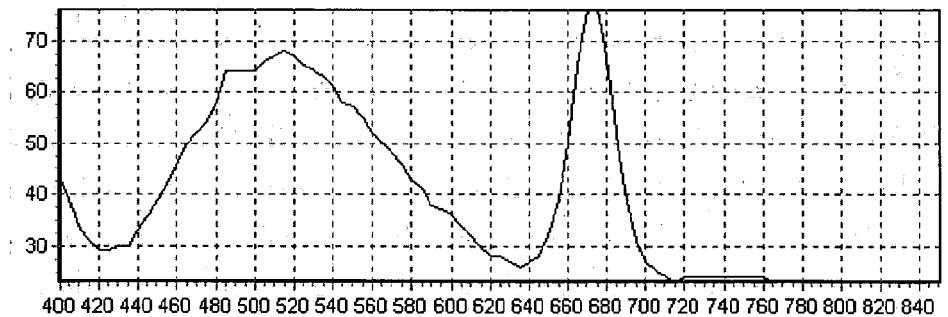
FIG. 3 represents the fluorescence spectrum of peanut oil when excited by a laser with a wave length of 405 nm.

FIG. 3 shows the fluorescence spectrum for peanut oil. One can observe that a first fluorescence peak is present with a maximum between 510 nm and 525 nm, whereas a second fluorescence peak is observed around a wave length of 670 nm.

Figure 4:
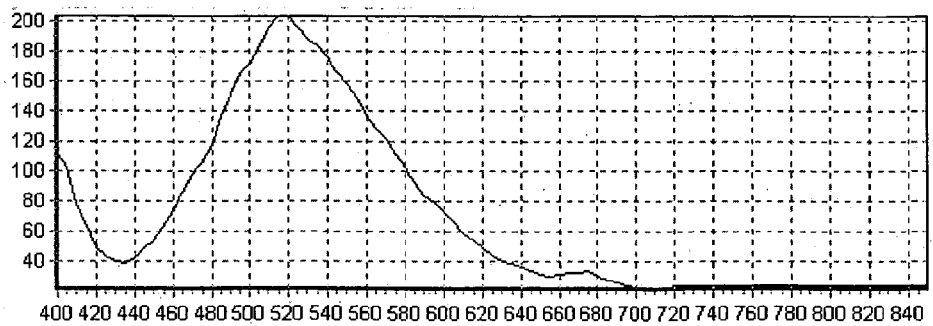
FIG. 4 represents the fluorescence spectrum of potato slices baked in peanut oil, in particular chips, when excited by a laser with a wave length of 405 nm.
Figure 5:
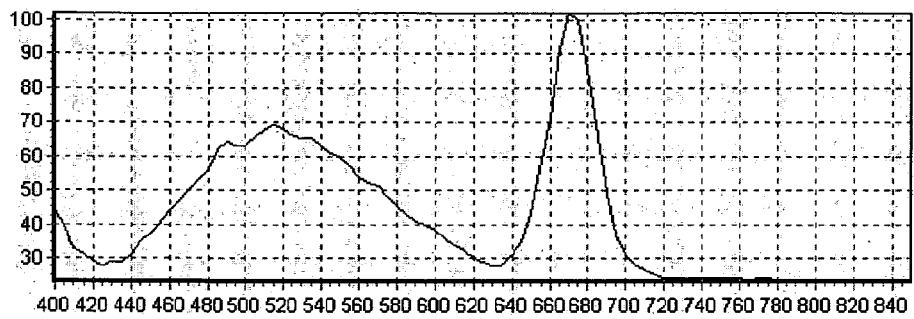
FIG. 5 represents the fluorescence spectrum of sunflower oil with a high olein content (HOSO) when excited by a laser with a wave length of 405 nm.
Figure 6:
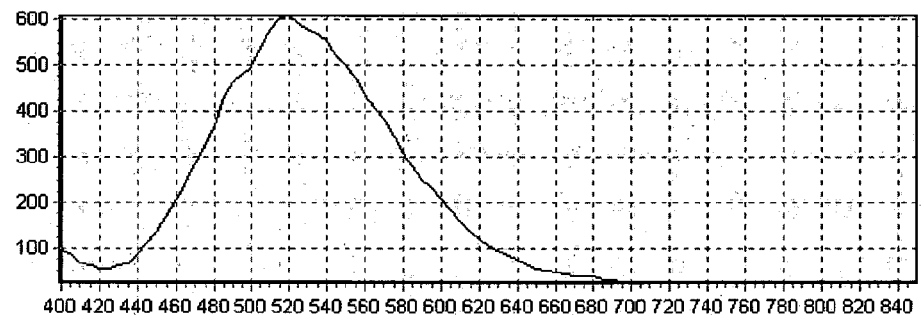
FIG. 6 represents the fluorescence spectrum of potato slices, in particular chips, baked in the oil of FIG. 5, when excited by a laser with a wave length of 405 nm.

When the fluorescence spectrum of thin potato slices without any flaws, baked in the peanut oil of FIG. 3, in particular of chips, is determined, it is found that there is a fluorescence peak around a wave length of 520 nm, whereas the fluorescence around the wave length of some 670 nm has become negligible, as is shown in FIG. 4.

Moreover, it turns out that this fluorescence peak around 520 nm has a relatively large intensity, as a result of which it can be easily detected. It is assumed that there is a certain interaction between the oil and the potato products, which has for a result that, by baking the potato products in the vegetable oil, the fluorescence peaks of the oil itself and of the raw potato reinforce one another.

In the case of flaws in the products baked in peanut oil, said fluorescence peak around a wave length of 520 nm is not present, nor as with strange components which might be present in the product flow.

Thus, unwanted products in a product flow of potato products baked in peanut oil are detected by detecting the absence of said fluorescence peak in a band between 480 and 580 nm, and when such a fluorescence peak is not present, by qualifying the product concerned as an undesirable product. During the sorting of the potato products, these unwanted products are thus removed from the product flow.

Figure 7:
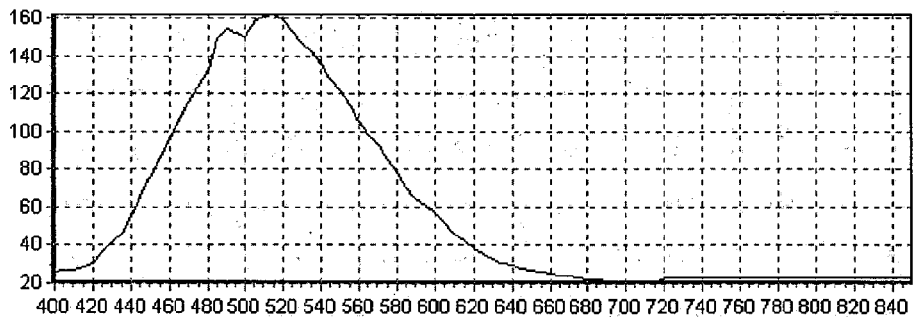
FIG. 7 represents the fluorescence spectrum of maize germ oil when excited by a laser with a wave length of 405 nm.
Figure 8:
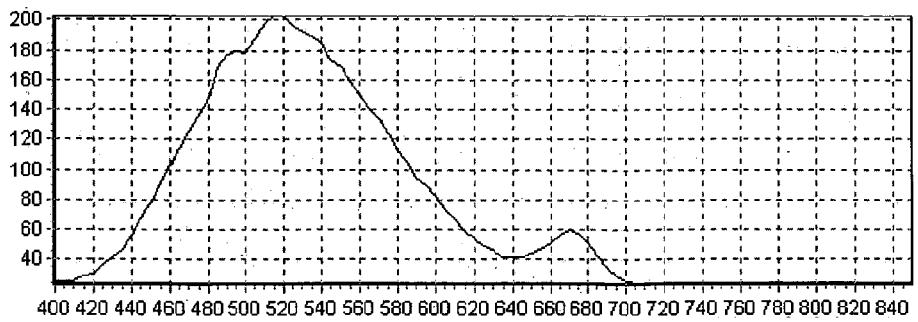
FIG. 8 represents the fluorescence spectrum of frying oil composed of a mixture of sunflower oil, rapeseed oil and palm olein when excited by a laser with a wave length of 405 nm.
Figure 9:
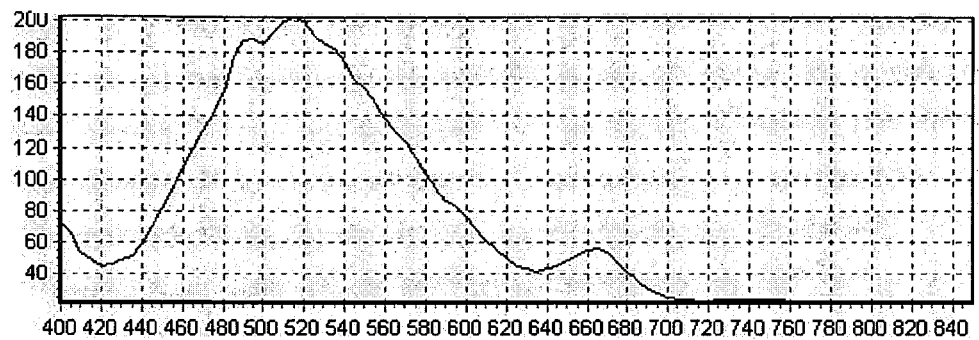
FIG. 9 represents the fluorescence spectrum of coleseed oil when excited by a laser with a wave length of 405 nm.
Figure 10:
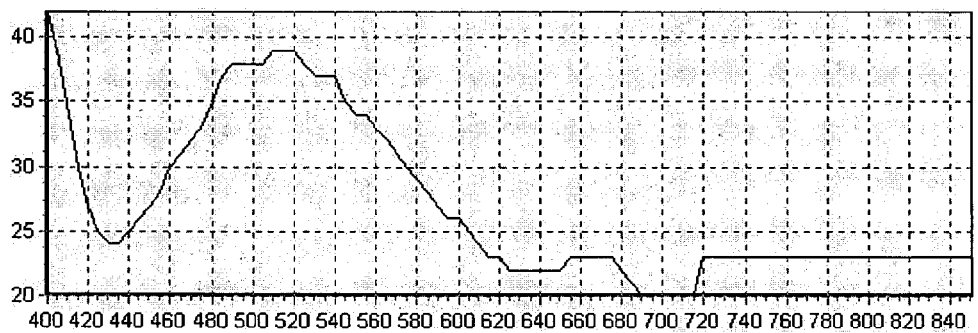
FIG. 10 represents the fluorescence spectrum of sunflower oil when excited by a laser with a wave length of 405 nm.
Figure 11:
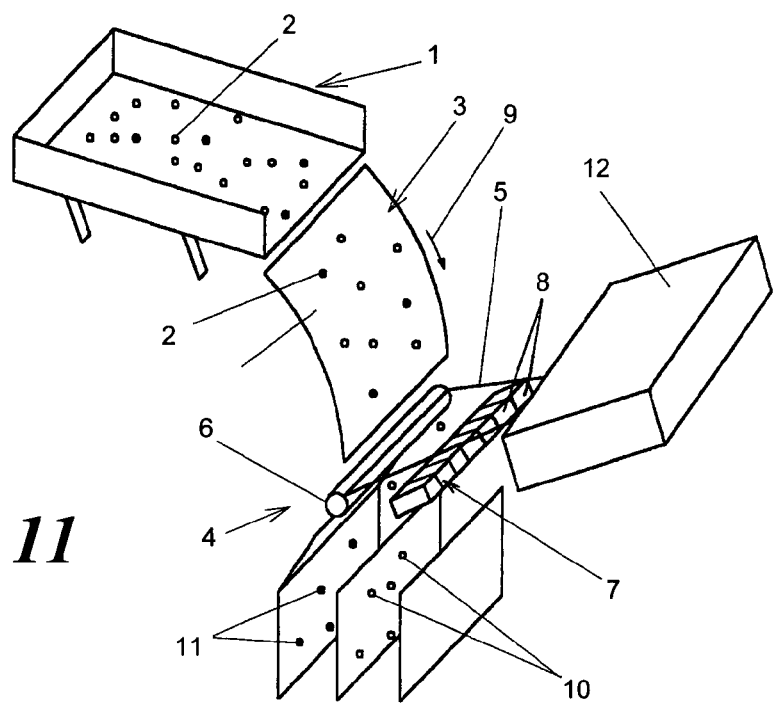
FIG. 11 is a schematic representation of a sorting machine, seen in perspective.
Figure 12:
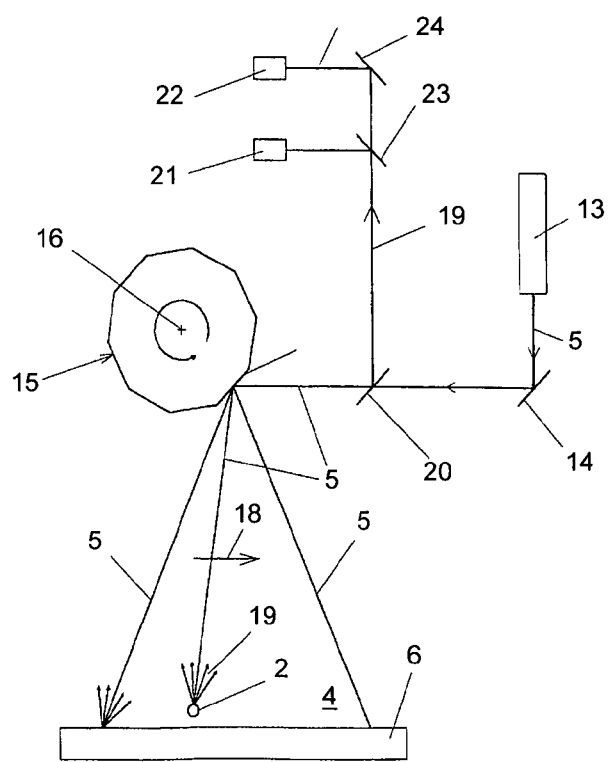
FIG. 12 is a schematic representation of a detection device for a sorting machine according to the invention.

FIG. 7 shows the fluorescence spectrum of sunflower oil having a high olein content (HOSO), whereas FIG. 8 represents the fluorescence spectrum of thin potato slices baked in said oil, in particular chips, showing no flaws.

These spectra indicate that the sunflower oil with a high olein content has a fluorescence peak at about 515 nm and around 670 nm. The latter fluorescence peak cannot be observed in the baked potato products, whereas a fluorescence peak with a very high intensity is observed for these baked products around 520 nm.

Flaws in the baked potato slices, which are baked in said sunflower oil with a high olein content, have no fluorescence peak in the band between 480 nm and 580 nm, such that in the absence of any fluorescence in this wave length band, a product will be qualified as an undesirable product and will preferably be removed from the product flow.

Thus, it is found that the fluorescence in a wave length band of 480 nm to 580 nm of potato products baked in sunflower oil with a high olein content is almost completely analogous to that of the potato products baked in peanut oil.

FIGS. 7 to 10 show the fluorescence spectra of maize germ oil, frying oil, coleseed oil and sunflower oil respectively, whereby the frying oil is composed of sunflower oil, rapeseed oil and palm olein.

All these fluorescence spectra have peaks in the wave length band of 480 to 580 nm. Consequently, potato products which have been baked in one of these vegetable oils are also sorted by detecting the presence of fluorescence in the detection band of 480 to 580 nm. When no fluorescence whatsoever is observed in this detection band, the product concerned will be qualified as an undesirable product and will be preferably removed from the product flow.

Further, the presence of glycoalkaloid, in particular of solanine, in the potato products is preferably detected as well. This is done by detecting fluorescence in a red light spectrum.

The presence of solanine sometimes becomes evident from a green discoloration of the potato product, but solanine may also be present without this green discoloration occurring.

The method according to the invention makes it possible to detect solanine irrespective of said discoloration.

In particular, the intensity of the light emitted by the potato products is detected in a band from 600 to 750 nm, in particular in a band from 600 to 700 nm, whereby a product will be qualified as a product containing solanine when a light intensity is detected in this band, resulting from the excitation by UV light, which exceeds a preset value. Such a product is then preferably removed from the product flow.

In an advantageous manner, the presence of a fluorescence peak having a wave length situated between 670 and 690 nm, in particular a wave length in the order of 680 nm, is thus detected. If such a fluorescence peak is present, a product will be qualified as a product containing glycoalkaloid, in particular solanine, and it will be removed from the product flow.

Figure 1:
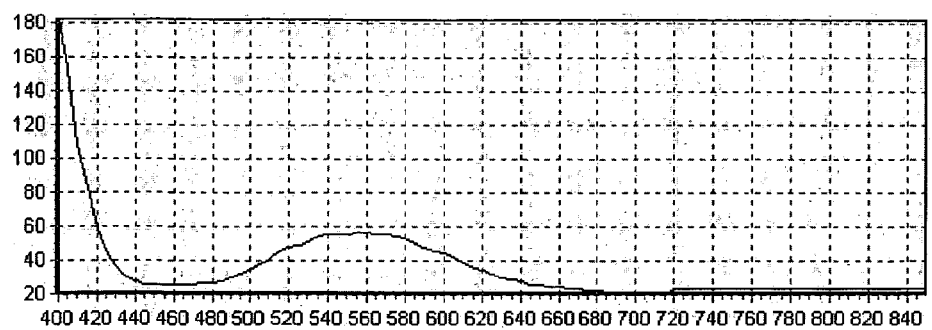
FIG. 1 represents the fluorescence spectrum of the flesh of a potato when excited by a laser with a wave length of 405 nm.

A possible embodiment of a sorting machine for applying the method according to the invention is represented in FIG. 1. This sorting machine is provided with a vibrating table 1 onto which the potato products 2 to be sorted are supplied. As a result of the vibrations of this vibrating table 1, the products 2 are led to a drop plate 3. Next, through the action of the gravitational force, the products 2 move over the surface of the drop plate 3 in a wide product flow with a thickness of about one product over practically its entire width, whereby they leave the drop plate 3 at its bottom edge. Subsequently, the products 2 move in free fall in a product flow through a detection zone 4 where they are scanned by a beam of light 5 moving crosswise over the product flow.

In the detection zone, the product flow with the potato products is moved over a background element 6 extending over the entire width of the product flow. The background element 6 has further been positioned in such a way that said light beam 5 scanning the product flow will strike said background element 6 when there is no product 2 in the path of the light beam 5.

Downstream the detection zone 4, the products 2 from the product flow move along a removal device 7 which makes it possible to remove unwanted products from the product flow. The removal device 7 is formed of a row of compressed air valves 8 extending parallel to the product flow and crosswise to the moving device 9 of the latter. When a product is thus qualified as an undesirable product, a compressed air valve 8 will be opened in a position which corresponds to that of the undesirable product, such that the latter, under the influence of the thus generated compressed air jet, will be blown out of the product flow. Thus is generated a product flow 10 which contains practically no unwanted products, as well as a flow separated from the latter containing practically only unwanted products 11.

Further, the sorting machine comprises a detection device 12 which makes it possible to generate said beam of light 5 and to detect the light emitted by the products 2 in said detection zone 4.

As is schematically represented in FIG. 4, said detection device comprises a light source 13 to generate the beam of light 5 with a wave length of 350 to 450 nm. This light source 13 is preferably formed of a laser source and thus generates a laser beam. The laser beam has for example a wave length of 378 nm or of 405 nm. The beam of light 5 is reflected as of the light source 13 via a mirror 14 to a polygon mirror 15 rotating around a central axis thereof. This polygon mirror 15 has successive mirror faces 17 on its perimeter. The beam of light 5 strikes the polygon mirror 15 and is directed, via one of its mirror faces 17, to the product flow and to said background element 6. As a result of the rotation of the polygon mirror, the beam of light 5 moves over the entire width of the product flow as indicated by arrow 18 and thus scans the products 2 to be sorted.

When the beam of light 5 strikes a product 2 to be sorted, this product will be excited by the beam of light 5 and it will fluoresce. The light 19 which is emitted as a result of this fluorescence is sent, via the polygon mirror 15 and a beam separator 20, to detectors 21 and 22 via respective semi-transparent mirrors 23 and 24.

A first detector 21 of these detectors is sensitive to green light having a wave length of for example 460 to 600 nm and generates a detection signal as a function of the observed light intensity which is emitted by a product 2 situated in the path of the light beam 5. This detector 21 co-operates with a control system to control the aforesaid removal device 7 when the light intensity observed by the detector 21 is lower than a preset value to thus remove the product concerned from the product flow. When said light intensity is lower than the preset value, no fluorescence peak will be observed in the detection band of 460 to 600 nm, and a product will consequently be qualified as an undesirable product.

A second detector 22 is sensitive to red light, in particular to light having a wave length of for example 600 to 700 nm, and preferably detects light having a wave length in the order of 680 nm. As a function of the observed light intensity, a detection signal is generated by this detector 22 in order to control said removal device 7. In particular, a product will be removed from the product flow by means of the removal device 7 when said intensity of the red light detected by the detector 22 exceeds a preset value. For, in this case, fluorescence is detected indicating the presence of solanine in the product situated in the path of the light beam.

Further, the background element 6 will emit light having a wave length which corresponds practically to said detection band when said beam of light strikes the background element 6. Thus is made sure that the compressed air valves 8 of the removal device 7 are only activated when an undesirable product is situated in the path of the light beam 5, and they will not be activated when there is no product 2 in the path of the light beam 5. In particular, the background element 6 will fluoresce when said beam of light strikes it, and it will preferably emit light having a wave length of 500 to 560 nm.

If the presence of solanine in the potato products is being detected as well according to the method of the invention, the background element 6 will be selected such that it will further not emit any light in a band of 600 nm to 700 nm, and preferably up to 750 nm, in particular in a band situated around 680 nm when it is hit by said beam of light 5.

Naturally, the invention is not restricted to the above-described embodiments of the method and the sorting machine for sorting potato products.

Thus, for example in the sorting machine, the vibrating table 1 and/or the drop plate 3 can be replaced by a conveyor belt for moving the products to be sorted to the detection zone.

Further, the wave length of the fluorescence peak for detecting flaws or strange components in the product flow may shift somewhat as a function of the wave length of the light beam which hits the products and excites them. Thus, the fluorescence peak for detecting the presence of solanine may shift as well as a function of the wave length of the exciting light beam.

Apart from that, it is clear that the detection of flaws or strange components in the product flow can be carried out completely independent from the detection of the presence of solanine.

The invention claimed is:

1. A method for sorting potato products which are being moved in a product flow through a detection zone, whereby unwanted products in the product flow are detected and separated from the product flow, comprising:
   in said detection zone, directing a beam of light having a wave length between 350 and 450 nm to said products,
   detecting intensity of the light which is emitted by the products in a detection band of 460 to 600 nm,
   detecting the presence of a fluorescence peak in said detection band, and
   qualifying a product as an undesirable product and separating said undesirable product from the product flow if said fluorescence peak is not present and said intensity is lower than a preset value, and
   maintaining a product in the product flow if the presence of said fluorescence peak is detected.

2. The method according to claim 1, wherein said detection band is situated between 480 and 580 nm and the presence of a fluorescence peak is detected in said detection band, wherein a product will be qualified as an undesirable product and will be separated from the product flow if said fluorescence peak is not present.

3. The method according to claim 1, wherein for the sorting of raw potato products, said detection band is situated between 540 and 570 nm and the presence of a fluorescence peak is detected in this detection band, and wherein a product will be qualified as an undesirable product and will be separated from the product flow if said fluorescence peak is not present.

4. The method according to claim 1, wherein for sorting potato products baked in vegetable oil, said detection band is situated between 480 and 580 nm and the presence of a fluorescence peak is detected in this detection band and wherein a product will be qualified as an undesirable product and will be separated from the product flow when said fluorescence peak is not present.

5. The method according to claim 1, wherein the presence of glycoalkaloid in said potato products is detected by detecting the intensity of the light emitted by the products in a band between 600 and 750 nm, wherein a product will be qualified as a product containing glycoalkaloid and will be removed from the product flow if said intensity is higher than a preset value.

6. The method according to claim 5, wherein the presence of a fluorescence peak having a wave length situated between 670 and 690 nm is detected and wherein a product will be qualified as a product containing glycoalkaloid and will be removed from the product flow if such a fluorescence peak is present.

7. The method according to claim 1, wherein said products are being moved through said detection zone in a wide product flow with a thickness of about one product, and wherein said beam of light is formed of a laser beam which is moved crosswise over the width of said product flow.

8. The method according to claim 7, wherein said laser beam has a wave length of approximately 365 nm.

9. The method according to claim 7, wherein said laser beam has a wave length of approximately 378 nm.

10. The method according to claim 7, wherein said laser beam has a wave length of approximately 405 nm.

11. The method according to claim 1, wherein said products are moved in the detection zone in front of a background element, said background element extending over the entire width of the product flow, such that said beam of light will strike this background element when there is no product situated in the beam of light, wherein the background element will emit light having a wave length which corresponds to said detection band when the background element is hit by said beam of light.

12. The method according to claim 1, wherein said products are moved in front of a background element in the detection zone, said background element extending over the entire width of the product flow, so that said beam of light will strike the background element when there is no product situated in the beam of light, wherein said background element emits practically no light in a band of 600 nm to 700 nm.

13. The method according to claim 11, whereby said background element will fluoresce when the beam of light strikes the background element, and will emit light having a wave length of 500 to 560 nm.

14. A method for detecting products containing glycoalkaloid in a product flow of potato products, comprising:
   making a beam of light with a wave length situated in a band of 350 to 450 nm strike said potato products,
   detecting intensity of light generated by fluorescence which is emitted by the products in a band of 600 to 750 nm,
   detecting the presence of a fluorescence peak having a wave length situated between 670 and 690 nm, and
   qualifying a product as a product containing glycoalkaloid when said intensity is higher than a preset value and a detected fluorescence peak is present.

15. The method according to claim 14, wherein the presence of a fluorescence peak having a wave length in the order of 680 nm is detected and wherein a product will be qualified as a product containing glycoalkaloid when such a fluorescence peak is present.

16. A sorting machine for sorting potato products comprising:
   a detection zone through which said potato products are moved in a product flow,
   a light source which generates a beam of light with a wave length situated in a band of 350 to 450 nm which strikes said products in the detection zone,
   a detector which is sensitive to green light having a wave length of 460 to 600 nm and which generates a detection signal as a function of the observed light intensity, and
   a control system that co-operates with said detector to detect a fluorescence peak and to control, responsive to said fluorescence peak, to maintain a product in the product flow if the presence of the fluorescence peak is detected, and to control a removal device for the removal of unwanted products from the product flow when said fluorescence peak is not present and the light intensity observed by the detector is lower than a preset value.

17. The sorting machine according to claim 16, wherein said detector is sensitive to light having a wave length of 480 to 580 nm.

* * * * *